US010288616B2

(12) United States Patent
Catenacci et al.

(10) Patent No.: US 10,288,616 B2
(45) Date of Patent: May 14, 2019

(54) QUANTIFYING MET PROTEIN FOR CANCER TREATMENT

(71) Applicant: Expression Pathology, Inc., Rockville, MD (US)

(72) Inventors: Daniel Catenacci, Chicago, IL (US); Todd Hembrough, Gaithersburg, MD (US); Fabiola Cecchi, Washington, DC (US); Wei-Li Liao, Herndon, VA (US)

(73) Assignees: Expression Pathology, Inc., Rockville, MD (US); The University Of Chicago, Chicago, IL (US)

( * ) Notice: Subject to any disclaimer, the term of this patent is extended or adjusted under 35 U.S.C. 154(b) by 0 days.

(21) Appl. No.: 15/276,686

(22) Filed: Sep. 26, 2016

(65) Prior Publication Data

US 2017/0097354 A1    Apr. 6, 2017

Related U.S. Application Data

(60) Provisional application No. 62/232,234, filed on Sep. 24, 2015.

(51) Int. Cl.
| | |
|---|---|
| A61K 45/06 | (2006.01) |
| C07K 16/22 | (2006.01) |
| C07K 16/28 | (2006.01) |
| A61K 39/395 | (2006.01) |
| G01N 33/574 | (2006.01) |

(52) U.S. Cl.
CPC .... *G01N 33/57446* (2013.01); *A61K 39/3955* (2013.01); *A61K 45/06* (2013.01); *C07K 16/22* (2013.01); *C07K 16/2863* (2013.01); *G01N 2333/4753* (2013.01); *G01N 2333/71* (2013.01); *G01N 2333/82* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 9,372,195 B2 * | 6/2016 | Krizman | G01N 33/4833 |
| 2012/0089541 A1 | 4/2012 | Patel et al. | |
| 2013/0029357 A1 | 1/2013 | Ise et al. | |
| 2013/0092079 A1 | 4/2013 | Austin et al. | |
| 2014/0005282 A1 | 1/2014 | Krizman et al. | |
| 2014/0234328 A1 * | 8/2014 | Anderson | G01N 33/57446 424/142.1 |

FOREIGN PATENT DOCUMENTS

| | | |
|---|---|---|
| CA | 2847245 A1 | 3/2013 |
| HK | 2014-507640 A | 3/2014 |
| JP | 2012-533738 A | 12/2012 |
| WO | 2011008990 A1 | 1/2011 |
| WO | 2011-125458 A1 | 10/2011 |
| WO | 2012092302 A1 | 7/2012 |
| WO | WO 2013/173627 * | 11/2013 |
| WO | 2014146139 A2 | 9/2014 |

OTHER PUBLICATIONS

Lee et al., Cancers 2014, 6, 2313-2329; doi:10.3390/cancers6042313.*
Catenacci, D et al.: "Absolute Quantitation of Met Using Mass Spectrometry for Clinical Application: Assay Precision, Stability, and Correlation with MET Gene Amplification in FFPE Tumor Tissue", PLOS ONE, Jul. 2014, vol. 9, Issue 7, pp. 1-14.
Guo, et al.: "Multidimensional identification of tissue biomarkers of gastric cancer", Journal Proteome Res., May 7, 2012, vol. 11, pp. 3405-3413.
Shah, M., et al.: "Phase II Study Evaluating 2 Dosing Schedules of Oral Foretinib (GSK1363089), cMET/VEGFR2 Inhibitor, in Patients with Metastatic Gastric Cancer", PLOS ONE, Mar. 2013, vol. 8, Issue 3, pp. 1-9.
Office Action issued in CA 2,999,895 dated Feb. 14, 2019.
Extended European Search Report issued in EP 16849880.6 dated Mar. 11, 2019.
Japanese Office Action dated Feb. 26, 2019 issued in Japanese Patent Application No. 2018-515596 with English translation, 7 pages.

* cited by examiner

*Primary Examiner* — Marianne P Allen
(74) *Attorney, Agent, or Firm* — Harness, Dickey and Pierce, P.L.C.

(57) ABSTRACT

Methods are provided for treating a gastric cancer patient. A specific Met fragment peptide is precisely quantitated by SRM-mass spectrometry directly in gastric tumor cells collected from gastric tumor tissue that was obtained from the cancer patient and compared to a reference level. If the Met peptide is below the reference level a second therapeutic regimen is used to treat the patient whereas if the Met peptide is above the reference level then a first therapeutic regimen combining, for example, the second regimen with one or more Met inhibitor therapeutic agents may be used to treat the patient.

11 Claims, 2 Drawing Sheets

Specification includes a Sequence Listing.

SEQUENCE LISTING

<160> NUMBER OF SEQ ID NOS: 1

<210> SEQ ID NO 1
<211> LENGTH: 9
<212> TYPE: PRT
<213> ORGANISM: Homo sapiens

<400> SEQUENCE: 1

Thr Glu Phe Thr Thr Ala Leu Gln Arg
1               5

QUANTIFYING MET PROTEIN FOR CANCER TREATMENT

This application claims priority to provisional application serial no. 62/232,234, filed Sep. 24, 2015, the contents of which are hereby incorporated by reference in its entirety. This application also contains a sequence listing submitted electronically via EFS-web, which serves as both the paper copy and the computer readable form (CRF) and consists of a file entitled "SEQ_LISTING_001152_8050_US01", which was created on Sep. 21, 2016, which is 407 bytes in size, and which is also incorporated by reference in its entirety.

INTRODUCTION

Improved methods are provided for treating cancer patients by quantitative assay of the Met protein in tumor tissue from such patients and identification of those patients most likely to respond to treatment with chemotherapeutic agents, including standard chemotherapeutic agents. In addition, patients identified as unlikely to respond to standard chemotherapeutic agents may potentially respond to treatment with a regimen that includes one or more anti-Met therapeutic agents. The level of Met expression in the tumor tissue is determined by quantitating a specified fragment peptide derived from subsequences of the full-length Met protein and this level is compared to a reference level. If the level of Met expression is higher than the reference level the patient may likely not respond to standard chemotherapy agents and may be treated with a regimen that includes at least one anti-Met therapeutic agent, whereas if the level is below the reference level the patient may likely respond to treatment with standard chemotherapeutic agents and is therefore treated with a regimen that does not include an anti-Met agent. Met is also referred to as hepatocyte growth factor receptor, proto-oncogene c-Met, HGF receptor, tyrosine-protein kinase Met, scatter factor receptor, and SF receptor.

The specified Met fragment peptide is detected using mass spectrometry-based Selected Reaction Monitoring (SRM), also referred to as Multiple Reaction Monitoring (MRM), and which is referred to herein as an SRM/MRM assay. An SRM/MRM assay is used to detect the presence and quantitatively measure the amount of the specified Met fragment peptide directly in cells procured from cancer patient tissue, for example formalin-fixed cancer tissue. Each molecule of fragment peptide is derived from one molecule of full-length Met and therefore measuring the amount of the fragment peptide allows quantitation of the amount of intact Met protein in the tumor sample. Specific and optimized therapeutic agents and treatment strategies can be used to treat an individual cancer patient's disease based on how much of the Met protein is present in the patient's cancer cells.

SUMMARY OF THE INVENTION

Methods are provided for treating a patient suffering from gastric cancer comprising detecting and quantitating a specified Met fragment peptide in a protein digest prepared from a tumor sample obtained from the patient and calculating the level of the Met peptide in said sample by selected reaction monitoring using mass spectrometry. The level of the Met fragment peptide is then compared to a reference level and the patient is treated based up on the result of this comparison. If the measured level of the Met fragment peptide level is above the reference level then the patient is treated with a first therapeutic regimen; whereas if it is below the reference level then the patient is treated with a second therapeutic regime. The second therapeutic regime may be a conventional therapeutic regime for treating gastric cancer, such as a regimen selected from the group consisting of cisplatin/5FU, FOLFOX, FOLFIRI, paclitaxel, 5FU, capecitabine, ECF, and DCF. The first therapeutic regimen advantageously includes a Met inhibitor and may also include one or more agents such as cisplatin, 5FU, leucovorin, oxaliplatin, irinotecan, paclitaxel, capecitabine, epirubicin, and docetaxel, or regimens including cisplatin/5FU, FOLFOX, FOLFIRI, paclitaxel, 5FU, capecitabine, ECF, and DCF. Met inhibitors that may be used include K252a, SU11274, PHA-665752, ARQ197, Foretinib, SGX523, MP470, truncated HGF, an anti-HGF neutralizing antibody, an uncleavable form of HGF, NK4; Decoy MET, cabozantinib, foretinib, onartuzumab (MetMab), DN30 (anti-c-Met monoclonal antibody), and combinations of these inhibitors. Similarly, immunotherapy using c-Met HTL epitopes has been described. See *OncaImmunology* 4:2, e976077; (February 2015). In addition, use of c-Met specific T-cells also has been described. See Thayaparan et al., *Cancer Immunol Res* 2016; 4(1 Suppl):Abstract nr A075.

The reference level against which the measured Met level is compared can be, for example: 400 amol/µg, +/−250 amol/µg; 400 amol/µg, +/−150 amol/µg; 400 amol/µg, +/−100 amol/µg; 400 amol/µg, +/−50 amol/µg; or 400 amol/µg, +/−25 amol/µg, of biological sample protein analyzed.

In these methods the protein digest can be a protease digest, such as a trypsin digest, and may be prepared by the "liquid tissue" protocol.

The mass spectrometry measurements may be carried out using a method such as tandem mass spectrometry, ion trap mass spectrometry, triple quadrupole mass spectrometry, MALDI-TOF mass spectrometry, MALDI mass spectrometry, hybrid ion trap/quadrupole mass spectrometry and time of flight mass spectrometry. The mode of mass spectrometry used may be, for example Selected Reaction Monitoring (SRM), Multiple Reaction Monitoring (MRM), and/or multiple Selected Reaction Monitoring (mSRM).

In the methods described above the specified Met peptide advantageously has the amino acid sequence as set forth as SEQ ID NO:1.

The tumor sample may be a cell, a collection of cells, or a solid tissue. Advantageously the tumor sample is formalin-fixed solid tissue, for example paraffin embedded tissue.

In these methods the specified Met peptide may be quantitated by comparison to a spiked internal standard peptide of known amount, where the native peptide in the biological sample and the internal standard peptide both have the same amino acid sequence as shown in SEQ ID NO:1. The internal standard peptide advantageously is an isotopically labeled peptide where the isotopes are, for example $^{18}O$, $^{17}O$, $^{15}N$, $^{13}C$, $^{2}H$ or combinations thereof.

Any of the methods described above may be used together with the detection and quantitation of other peptides. This allows the analysis and quantitation of other proteins, together with Met, in a multiplex format.

DETAILED DESCRIPTION

Figure 1:
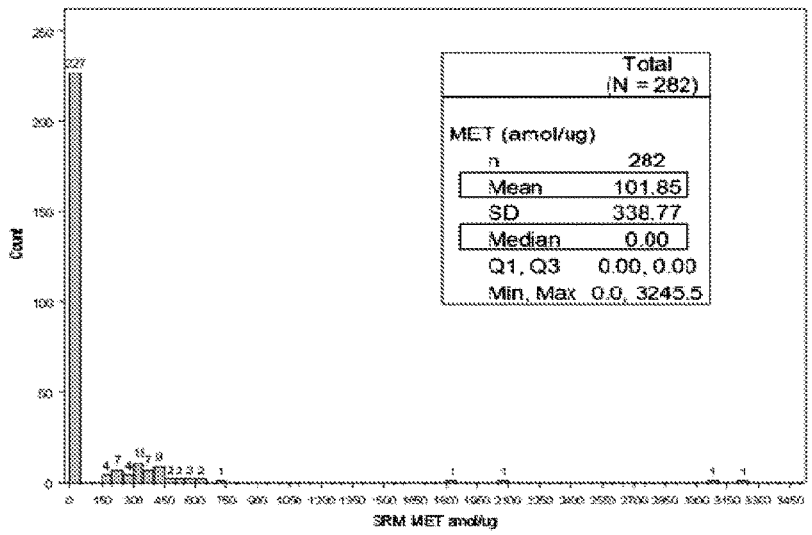
FIG. 1: Quantitative distribution of Met-SRM (amol/ug protein analyzed) across 282 gastric cancer patient tissue samples.

Improved methods of treating cancer are provided which allow for determining the likely clinical course of cancer in a patient and, more specifically, whether or not the patient will or will not clinically respond in a favorable manner (prognosis) to standard chemotherapeutic agents and regimens such as cisplatin/5FU, FOLFOX, FOLFIRI, paclitaxel, 5FU, capecitabine, ECF, and/or DCF. As part of the technology described herein, diagnostic methods for measuring Met protein in a tumor sample or samples from the patient are provided. The tumor sample advantageously is formalin-fixed.

Using an SRM/MRM assay that measures a specific Met peptide fragment, and particular characteristics about this peptide, the amount of Met in cells derived from formalin-fixed paraffin embedded (FFPE) tissue is determined. The peptide fragment derives from the extracellular domain of the full-length Met protein and has the sequence TEFTTALQR. Surprisingly it has been found that this peptide can be reliably detected and quantitated in digests prepared from FFPE samples of tumor tissue. See U.S. Pat. No. 13,976,956, (now U.S. Pat. No. 9,372,195) the contents of which are hereby incorporated by reference in their entirety. Once the amount of Met protein has been determined, that amount is compared to a reference level and the comparison is used to select and administer an improved or optimized treatment regimen for the patient.

More specifically, this SRM/MRM assay can measure the fragment peptide directly in complex protein lysate samples prepared from cells procured from patient tissue samples, such as formalin-fixed cancer patient tissue. Methods of preparing protein samples from formalin-fixed tissue are described in U.S. Pat. No. 7,473,532, the contents of which are hereby incorporated by reference in their entirety. The methods described in U.S. Pat. No. 7,473,532 may conveniently be carried out using Liquid Tissue reagents and protocols available from Expression Pathology Inc. (Rockville, Md.). An exemplary protocol is provided below in Example 1.

The most widely and advantageously available form of tissue, and cancer tissue, from cancer patients is formalin-fixed, paraffin embedded tissue. Formaldehyde/formalin fixation of surgically removed tissue is by far the most common method of preserving cancer tissue samples worldwide and is the accepted convention in standard pathology practice. Aqueous solutions of formaldehyde are referred to as formalin. "100%" formalin consists of a saturated solution of formaldehyde (about 40% by volume or 37% by mass) in water, with a small amount of stabilizer, usually methanol, to limit oxidation and degree of polymerization. The most common way in which tissue is preserved is to soak whole tissue for extended periods of time (8 hours to 48 hours) in aqueous formaldehyde, commonly termed 10% neutral buffered formalin, followed by embedding the fixed whole tissue in paraffin wax for long term storage at room temperature. Thus molecular analytical methods to analyze formalin-fixed cancer tissue will be the most accepted and heavily utilized methods for analysis of cancer patient tissue.

Results from the SRM/MRM assay can be used to correlate accurate and precise quantitative levels of the Met protein within the specific cancer of the patient from whom the tissue was collected and preserved. This not only provides diagnostic information about the cancer, but also provides prognostic information about whether or not the patient from whom the cancer tissue was obtained will respond in a favorable way to standard chemotherapeutic agents and regimens or may also likely respond to therapy with anti-cancer therapeutic agents designed to specifically inhibit the function and/or reduce the presence of the Met protein. Standard chemotherapeutic agents and regimens include cisplatin/5FU, FOLFOX (leucovorin, 5-FU and oxaliplatin), FOLFIRI (leucovorin, 5-FU and irinotecan), paclitaxel, 5FU, capecitabine, ECF (epirubicin, cisplatin, and 5-FU), and/or DCF (docetaxel, cisplatin and 5-FU). Anti-cancer therapeutic agents designed to specifically inhibit the function and/or reduce the presence of the Met protein include: MET kinase inhibitors such as K252a (Fermentek Biotechnology), SU11274 (SUGEN), PHA-665752 (Pfizer), ARQ197 (ArQule), Foretinib (XL880, Exelixis), SGX523 (SGX Pharmaceuticals), cabozantinib (Exelixis), and MP470 (SuperGen); HGF inhibitors include truncated HGF, anti-HGF neutralizing antibodies such as AV299 (AVEO), and AMG102 (Amgen), uncleavable forms of HGF, and NK4; and Decoy MET (a soluble truncated MET receptor) and combinations of these inhibitors. Monoclonal antibodies include onartuzumab (MetMab)(Roche), DN30 (anti-c-Met monoclonal antibody)(see Proc. Nat'l Acad. Sci., 103:5090 (2006)), Similarly, active immunotherapy using c-Met HTL epitopes (*OncaImmunology* 4:2, e976077; (February 2015)) and c-Met specific T-cells (*Cancer Immunol Res* 2016; 4(1 Suppl):Abstract nr A075) also has been described.

Treating cancer patients with standard chemotherapeutic agents and regimens such as those described above has been routine for years and decades with success in many cases, and in particular in cases of gastric cancer. However, up to the present time there has been no test that has allowed a clinician to predict the likelihood that a cancer patient will respond clinically to treatment with one of the agents or regimens or that has provided objective guidance to a physician as to the preferred course of treatment.

Many times the above-described treatment agents and regimens fail to prolong the life of cancer patients. As described below it has been found that lack of success in using such agents and/or regimens is associated with the situation when the Met protein is found to be aberrantly expressed at high levels. The Met protein is a signal receptor protein on many types of cells and, normally, Met receptors help control how a healthy cell grows, divides, and repairs itself. However, in some cancers, including gastric cancers, the cancer cells make too many Met receptors (Met protein overexpression), which makes the cells grow and divide in an uncontrolled way. In many cases this protein overexpression is accompanied by a Met gene that has been amplified, resulting in too many copies of the gene (known as Met gene amplification), which in turn can lead to expression of too many Met receptors (Met protein overexpression). The methods described herein permit a clinician to determine the level of Met protein in a patient's cancer cells and, based on that level, treat the patient with a therapeutic regimen that has the highest likelihood of success. More specifically, the methods provide an objective treatment regime for treating a patient either with standard chemotherapeutic agents and regimens or with a regimen that includes one or more anti-Met therapeutic agents.

Prior to the methods described herein, two basic tests were available for determining if a cancer, and especially a gastric cancer, may be expressing or overexpressing Met. Both tests use thin sections of tumor samples from a patient. The immunohistochemistry (IHC) test utilizes an antibody to detect the Met protein and strives to determine if there is too much Met protein in the cancer cells. The results of the IHC test can be: 0 (negative), 1+ (also negative), 2+ (borderline), or 3+ (positive-Met protein overexpression). The FISH (Fluorescence In Situ Hybridization) test seeks to measure if there are too many copies of the Met gene in the cancer cells. The results of the FISH test can be positive (Met gene amplification) or negative (no Met gene amplification). This FISH test infers that Met gene amplification results in over-expression of Met protein. Gastric cancers with Met gene amplification and/or Met protein overexpression are called Met-positive in pathology reports. Met-positive gastric cancers tend to grow faster and are more likely to spread and recur compared to Met-negative gastric cancers.

Research has shown that Met status test results using IHC and FISH may be unreliable or even wrong. This is likely because of a lack of objective and agreed-upon criteria between different labs, which use different rules for classifying positive and negative Met status. Each pathologist running these tests also may use different criteria to decide whether the results are positive or negative. In most cases, this happens when the test results are borderline, meaning that the results are neither strongly Met-positive nor Met-negative. In other cases, tissue from one area of a gastric cancer can test Met-positive while tissue from a different area of the cancer tests Met-negative. Inaccurate Met test results may mean that patients diagnosed with gastric cancer fail to receive the best possible care and may receive treatment that is ineffective and is accompanied by severe undesirable side effects.

The methods described herein provide improved methods of treatment that involve objective measurement of quantitative levels of the Met protein in tumors, especially gastric tumors, together with guidance regarding the levels of Met that are predictive of a patient's likely response to treatment. In this way the patient is provided with optimum therapy.

Detection of peptides and determining quantitative levels of a specified Met fragment peptide are determined in a mass spectrometer by the SRM/MRM methodology, whereby the SRM/MRM signature chromatographic peak area of each peptide is determined within a complex peptide mixture present in a Liquid Tissue lysate (see U.S. Pat. No. 7,473,532, as described above). Quantitative levels of the Met protein are then determined by the SRM/MRM methodology whereby the SRM/MRM signature chromatographic peak area of an individual specified peptide from the Met protein in one biological sample is compared to the SRM/MRM signature chromatographic peak area of a known amount of a "spiked" internal standard for the individual specified Met fragment peptide. In one embodiment, the internal standard is a synthetic version of the same exact Met fragment peptide that contains one or more amino acid residues labeled with one or more heavy isotopes. Such isotope labeled internal standards are synthesized so that mass spectrometry analysis generates a predictable and consistent SRM/MRM signature chromatographic peak that is different and distinct from the native Met fragment peptide chromatographic signature peak and which can be used as a comparator peak. Thus when the internal standard is spiked in known amounts into a protein or peptide preparation from a biological sample and analyzed by mass spectrometry, the SRM/MRM signature chromatographic peak area of the native peptide is compared to the SRM/MRM signature chromatographic peak area of the internal standard peptide, and this numerical comparison indicates either the absolute molarity and/or absolute weight of the native peptide present in the original protein preparation from the biological sample. Quantitative data for fragment peptides are displayed according to the amount of protein analyzed per sample.

Although SRM/MRM assays can be developed and performed on any type of mass spectrometer, including a MALDI, ion trap, or triple quadrupole, presently the most advantageous instrument platform for SRM/MRM assay is often considered to be a triple quadrupole instrument platform. In order to develop a mass spectrometric SRM/MRM assay for the Met fragment peptide additional information beyond simply the peptide sequence may be used. This additional information is important in directing and instructing the mass spectrometer, (e.g., a triple quadrupole mass spectrometer) to perform the correct and focused analysis of the specified Met fragment peptide. The additional information provides the triple quadrupole mass spectrometer with the correct directives to allow analysis of a single isolated target peptide within a complex lysate that may consist of hundreds of thousands to millions of individual peptides from all the proteins contained within a cell. The additional information about target peptides in general, and in particular about the specified Met fragment peptide, may include one or more of: the monoisotopic mass of each peptide; its precursor charge state; the precursor m/z value; the m/z transition ions; and the ion type of each transition ion. The peptide sequence of this specified Met fragment peptide and the necessary additional information as described for this specified Met fragment peptide is shown in Table 1.

TABLE 1

| SEQ ID | Peptide sequence | Mono Isotopic Mass | Precursor Charge State | Precursor m/z | Transition m/z | Ion Type |
|---|---|---|---|---|---|---|
| SEQ ID NO: 1 | TEFTTALQR | 1241.6599 | 2 | 533.78 | 588.346 | y5 |
| | | | 2 | 533.78 | 689.394 | y6 |
| | | | 2 | 533.78 | 836.462 | y7 |

To determine an appropriate reference level for Met quantitation, tumor samples are obtained from a cohort of patients suffering from gastric cancer and that have been treated with standard chemotherapeutic agents and regimens such as cisplatin/5FU, FOLFOX, FOLFIRI, paclitaxel, 5FU, capecitabine, ECF, and/or DCF. The tumor samples are formalin-fixed using standard methods and the level of Met in the samples is measured using the methods as described above. The tissue samples may also be examined using IHC and FISH using methods that are well known in the art. The patients in the cohort are treated with standard chemotherapeutic agents and regimens such as cisplatin/5FU, FOLFOX, FOLFIRI, paclitaxel, 5FU, capecitabine, ECF, and/or DCF and the response of the patients is measured using methods that are well known in the art, for example by recording the overall survival of the patients at time intervals after treatment. A suitable reference level can be determined using statistical methods that are well known in the art, for example by determining the lowest p value of a log rank test. Suitable statistical methods are described in Example 1 below.

Once a reference level has been determined it can be used to identify those patients whose Met expression level is high enough that they are unlikely to benefit from treatment with standard chemotherapeutic agents and regimens such as cisplatin/5FU, FOLFOX, FOLFIRI, paclitaxel, 5FU, capecitabine, ECF, and/or DCF. The reference level also can be used to identify those patients whose Met expression level is sufficiently low that treatment with standard chemotherapeutic agents and regimens such as cisplatin/5FU, FOLFOX, FOLFIRI, paclitaxel, 5FU, capecitabine, ECF, and/or DCF is likely to be of therapeutic benefit. The skilled artisan will recognize that anti-Met agents can also be used as part of a treatment regimen in patients whose Met levels are sufficiently high.

Levels of Met in patient's samples typically are expressed in amol/μg, although other units can be used. The skilled artisan will recognize that a reference level can be expressed as a range around a central value, for example, +/−250, 150, 100, 50 or 25 amol/μg. In the specific example described in detail below a suitable reference level was found to be 400 amol/μg or about 400 amol/μg, but the skilled artisan will recognize that levels higher or lower than this can be selected based on clinical results and experience.

Because both nucleic acids and protein can be analyzed from the same Liquid Tissue biomolecular preparation it is possible to generate additional information about disease diagnosis and drug treatment decisions from the nucleic acids in the same sample upon which proteins were analyzed. For example, if the Met protein is expressed by certain cells at increased levels, when assayed by SRM the data can provide information about the state of the cells and their potential for uncontrolled growth, potential drug resistance and the development of cancers can be obtained. At the same time, information about the status of the Met genes and/or the nucleic acids and proteins they encode (e.g., mRNA molecules and their expression levels or splice variations) can be obtained from nucleic acids present in the same Liquid Tissue biomolecular preparation can be assessed simultaneously to the SRM analysis of the Met protein. Any gene and/or nucleic acid not from the Met and which is present in the same biomolecular preparation can be assessed simultaneously to the SRM analysis of the Met protein. In one embodiment, information about the Met protein and/or one, two, three, four or more additional proteins may be assessed by examining the nucleic acids encoding those proteins. Those nucleic acids can be examined, for example, by one or more, two or more, or three or more of: sequencing methods, polymerase chain reaction methods, restriction fragment polymorphism analysis, identification of deletions, insertions, and/or determinations of the presence of mutations, including but not limited to, single base pair polymorphisms, transitions, transversions, or combinations thereof.

It also is possible to detect and quantitate peptides derived from other proteins in the same digest. This provides a clinician with additional information that can be used in the treatment of disease in a patient. For example, other proteins that can be detected and quantitated in the digest together with Met include proteins where aberrant expression of those proteins is known to be associated with cancer. Examples include proteins such as EGFR, IGF-1R, SPARC, HER-2, HER-3, HER-4, Bcl-2, ALK, K-ras, insulin receptor, PDGFR, PD-L1 and the like. The peptides from the different proteins can be detected and quantitated in a multiplex format, such as that described in U.S. Pat. Nos. 7,906,301 and 8,293,485, the contents of which are hereby incorporated by reference in their entirety.

Example 1: Determination of a Predictive Value of MET Protein Expression Levels for Prognosis of Gastric Cancer Patients Treated with Standard Chemotherapeutic Agents and Regimens Such as Cisplatin/5FU, FOLFOX, FOLFIRI, Paclitaxel, 5FU, Capecitabine, ECF, and/or DCF Patients 282 patients from United States (University of Chicago) and Italy (Universitá di Urbino) were identified with histologically confirmed primary and/or metastatic gastric cancer. Formalin-fixed, paraffin-embedded (FFPE) biopsies were collected prior to treatment. After surgery all patients were treated with one of the following standard chemotherapy regimens commonly used for gastric cancer: cisplatin/5FU, FOLFOX, FOLFIRI, paclitaxel, 5FU, capecitabine, ECF, and/or DCF.

Methods

Met was analyzed by mass spectrometry-SRM. FFPE tumor tissue was microdissected and solubilized for downstream mass spectrometry analysis using the liquid tissue protocol. An exemplary protocol is provided below. Met protein levels were quantitated using selected reaction monitoring mass spectrometry (SRM-MS). Spearman's rank correlation coefficient was used to assess correlations between parameters. Cox proportional hazards models, Kaplan-Meier estimates, and multivariate analysis were applied to explore relationships between Met and overall survival.

Preparation of a Lysate from a Formalin-Fixed Sample (Exemplary "Liquid Tissue" Protocol)

1. Place one 2 mm diameter by 25 μm thick section from a tissue punch into a silanized or low protein binding 1.5 ml microcentrifuge tube.
2. Add 500 μl of 20 mM Tris-HCl pH 7.8.
3. Heat at 95° C. for 1 minute.
4. Mix gently on a vortex mixer.
5. Carefully, without disturbing the tissue section, remove the buffer using a pipettor.
6. Add 750 μl of 20 mM Tris-HCl pH 7.8.
7. Heat at 95° C. for 1 minute.
8. Carefully, without disturbing the tissue section, remove the buffer using a pipettor.
9. Microcentrifuge at 10,000 rpm for 1 minute.
10. Remove any residual buffer from the microcentrifuge tube with a pipettor.

11. Add 10 μl of reaction buffer (10 mM Tris-HCl pH 7.8, 1.5 mM EDTA, 0.1% Triton X-100, 10% glycerol) to the tube. Make sure that the tissue is at the bottom of the tube and covered with reaction buffer.

12. Heat at 95° C. for 1.5 hours. Every 20 minutes, check the tube and shake the buffer that has formed a condensation in the cap down to the bottom of the tube so that it covers the tissue section before placing the tube back into the heating block.

13. Microcentrifuge at 10,000 rpm for 1 minute.

14. Place tubes on ice to cool.

15. Add 0.5 μl of 1% Trypsin and gently mix.

16. Incubate for 1 hour at 37° C. Every 20 minutes check the tube and shake the buffer that has formed a condensate in the cap down to the bottom of the tube. Vortex rigorously for 10 to 15 seconds. Shake the buffer down to the bottom of the tube so that it covers the tissue section before placing the tube back into the waterbath.

17. Microcentrifuge at 10,000 rpm for 1 minute.

18. Heat at 95° C. for 5 minutes.

19. Microcentrifuge at 10,000 rpm for 1 minute.

The resulting multi-use biomolecule lysate may be either used in subsequent assays or stored at −20° C. until ready for use.

Results

Figure 2:
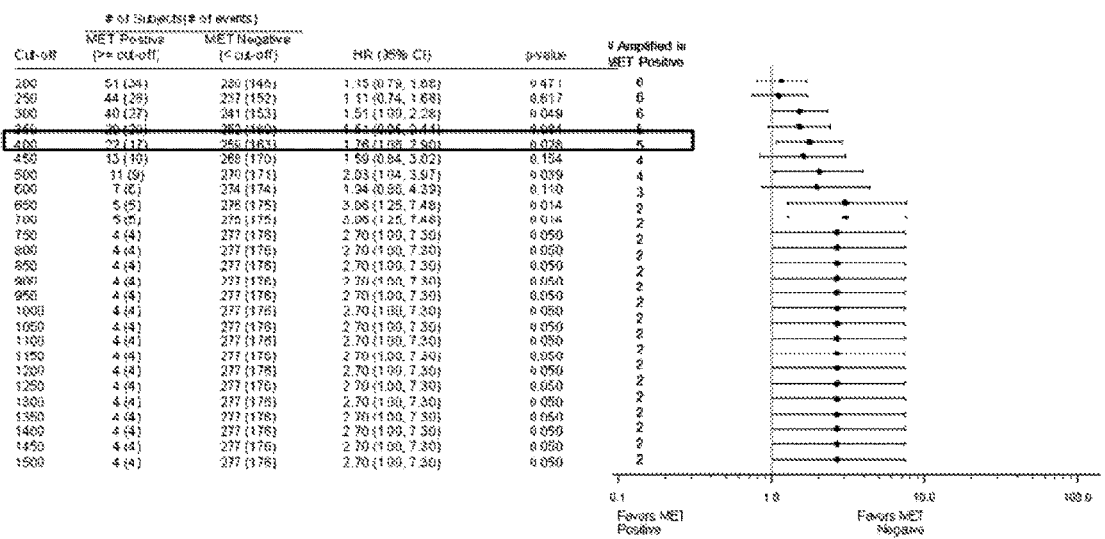
FIG. 2: Forest Plot Summarizing Results from Cox PH Model Evaluating Effect of Met-SRM on OS. Met-SRM assay has the strongest significant effect on OS at cutoff level 400 amol/μg.
Figure 3:
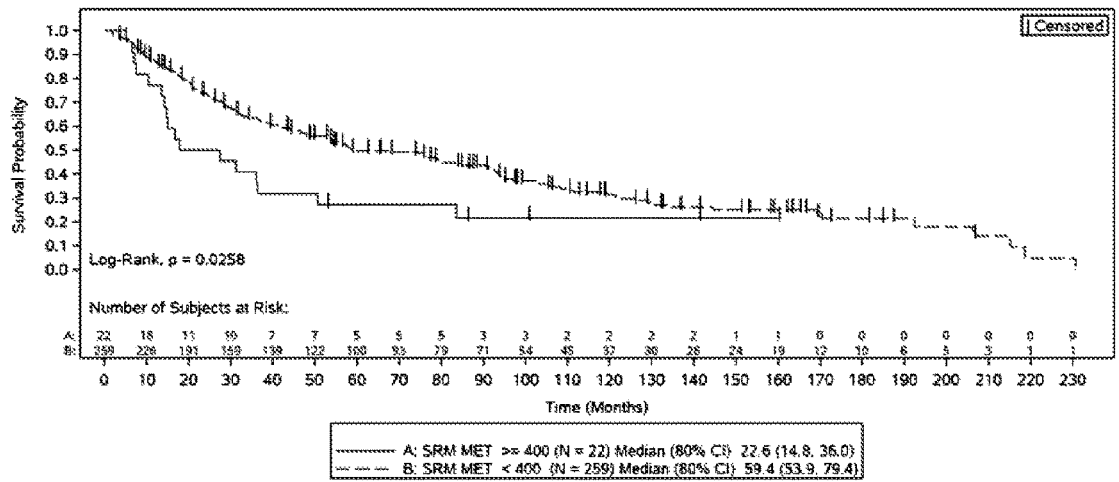
FIG. 3: Kaplan-Meier Plot of OS by Met-SRM Status. Median survival at the 400 amol/μg cutoff Met-SRM value was 22.6 months for Met-positive patients vs 59.4 months for Met-negative patients.
Figure 4:
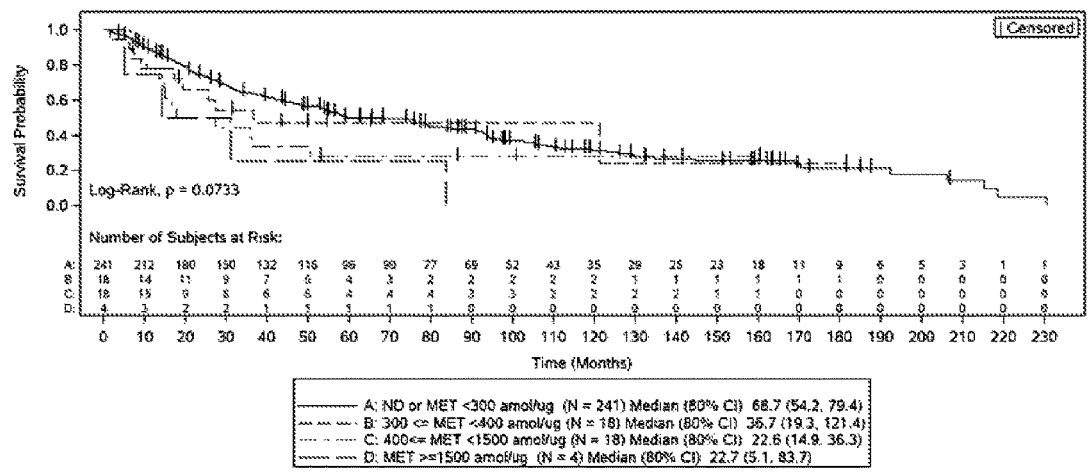
FIG. 4: Kaplan-Meier Plot of OS by Met-SRM across a range (4 categories) of assay values. Highest Met-SRM level indicates least-favorable prognosis for gastric cancer patients.

FIGS. 1-4 demonstrate that the Met-SRM assay provides prognostic value for overall survival of gastric cancer patients treated with the standard chemotherapeutic regimens of cisplatin/5FU, FOLFOX, FOLFIRI, paclitaxel, 5FU, capecitabine, ECF, and/or DCF.

The invention claimed is:

1. A method of treating a patient suffering from gastric cancer comprising:
   (a) detecting and quantitating a specified Met fragment peptide in a protein digest prepared from a tissue sample and calculating the level of the Met peptide in said sample by selected reaction monitoring using mass spectrometry, wherein said specified Met peptide has the amino acid sequence as set forth as SEQ ID NO:1, wherein said tissue sample is formalin-fixed tissue prepared from a tumor sample obtained from the patient
   (b) comparing the level of said Met fragment peptide to a reference level, and
   (c) treating said patient with a first therapeutic regimen comprising at least one agent targeted at Met if the level of said Met fragment peptide level is above said reference level or treating said patient with a second therapeutic regimen comprising at least one regimen selected from the group consisting of cisplatin/5FU, FOLFOX, FOLFIRI, paclitaxel, 5FU, capecitabine, ECF, and DCF if said Met fragment peptide level is below said reference level, and wherein said reference level is selected from the group consisting of: 400 amol/μg, +/−25 amol/μg, of biological sample protein analyzed.

2. The method of claim 1 wherein said first therapeutic regimen further comprises at least one agent selected from the group consisting of cisplatin, 5FU, leucovorin, oxaliplatin, irinotecan, paclitaxel, capecitabine, epirubicin, and docetaxel.

3. The method of claim 1 wherein said first therapeutic regimen further comprises at least one regimen selected from the group consisting of cisplatin/5FU, FOLFOX, FOLFIRI, paclitaxel, 5FU, capecitabine, ECF, and DCF.

4. The method of claim 1 wherein said agent targeted at Met is selected from the group consisting of: Met inhibitors, selected from the group consisting of K252a, SU11274, PHA-665752, ARQ197, Foretinib, SGX523, MP470, truncated HGF, an anti-HGF neutralizing antibody, an uncleavable form of HGF, NK4, and Decoy MET; an anti-c-Met monoclonal antibody; and c-Met specific T-cells.

5. The method of claim 1, wherein said protein digest comprises a protease digest.

6. The method of claim 5, wherein said protein digest comprises a trypsin digest.

7. The method of claim 1, wherein said mass spectrometry comprises a method selected from the group consisting of tandem mass spectrometry, ion trap mass spectrometry, triple quadrupole mass spectrometry, MALDI-TOF mass spectrometry, MALDI mass spectrometry, hybrid ion trap/quadrupole mass spectrometry and time of flight mass spectrometry.

8. The method of claim 1, wherein the tissue is paraffin embedded tissue.

9. The method of claim 1, wherein detecting and quantitating the specified Met fragment peptide comprises determining the amount of the Met peptide in said sample by comparing to a spiked internal standard peptide of known amount, wherein both the native peptide in the biological sample and the internal standard peptide corresponds to the same amino acid sequence of the Met fragment peptide as shown in SEQ ID NO:1.

10. The method of claim 9, wherein the internal standard peptide is an isotopically labeled peptide.

11. The method of claim 10, wherein the isotopically labeled internal standard peptide comprises one or more heavy stable isotopes selected from $^{18}O$, $^{17}O$, $^{15}N$, $^{13}C$, $^{2}H$ or combinations thereof.

* * * * *